United States Patent
Belz et al.

(10) Patent No.: US 12,174,125 B2
(45) Date of Patent: Dec. 24, 2024

(54) FLOW CELL SYSTEM FOR OPTICAL FLUID ANALYSIS AND BIOREACTOR SYSTEM

(71) Applicant: World Precision Instruments Germany GmbH, Friedberg (DE)

(72) Inventors: Mathias Belz, Florstadt (DE); Philipp Raithel, Florstadt (DE); Dörte Solle, Hannover (DE); Tobias Steinwedel, Ronnenberg (DE)

(73) Assignee: World Precision Instruments Germany GmbH, Friedberg (DE)

( * ) Notice: Subject to any disclaimer, the term of this patent is extended or adjusted under 35 U.S.C. 154(b) by 395 days.

(21) Appl. No.: 17/262,363

(22) PCT Filed: Sep. 4, 2020

(86) PCT No.: PCT/EP2020/074866
§ 371 (c)(1),
(2) Date: Jan. 22, 2021

(87) PCT Pub. No.: WO2021/094009
PCT Pub. Date: May 20, 2021

(65) Prior Publication Data
US 2022/0205925 A1  Jun. 30, 2022

Related U.S. Application Data

(60) Provisional application No. 62/935,221, filed on Nov. 14, 2019.

(51) Int. Cl.
*G01N 21/85* (2006.01)
*C12M 1/00* (2006.01)
(Continued)

(52) U.S. Cl.
CPC ............. *G01N 21/82* (2013.01); *C12M 23/28* (2013.01); *C12M 41/00* (2013.01);
(Continued)

(58) Field of Classification Search
None
See application file for complete search history.

(56) References Cited

U.S. PATENT DOCUMENTS

| | | | | |
|---|---|---|---|---|
| 3,684,386 A | * | 8/1972 | Noll | G01N 21/05 359/232 |
| 2009/0145202 A1 | * | 6/2009 | Tokhtuev | G01N 21/79 356/246 |

(Continued)

FOREIGN PATENT DOCUMENTS

WO  2014146147 A2  9/2014

OTHER PUBLICATIONS

International Search Report and Written Opinion mailed Dec. 8, 2020 for International Patent Application No. PCT/EP2020/074866.

*Primary Examiner* — Rufus L Phillips
(74) *Attorney, Agent, or Firm* — Alix, Yale & Ristas, LLP

(57) ABSTRACT

A flow cell system for an optical fluid analysis comprises a disposable flow cell having at least one flow chamber comprising a fluid pathway, and at least one pair of opposed light transmitting windows along the fluid pathway, an external flow cell holder for holding the flow cell, at least one light source, and an external detection device couplable with at least one of the flow cell holder and the flow cell for bringing the external detection device in optical communication with the flow cell, the device having at least one optical detection unit. The external detection device is configured to conduct optical measurements of the fluid that flows in the flow cell through at least one pair of windows from externally under illumination by the at least one light source.

13 Claims, 7 Drawing Sheets

(51) Int. Cl.
  *C12M 1/34*  (2006.01)
  *G01N 21/03* (2006.01)
  *G01N 21/05* (2006.01)
  *G01N 21/31* (2006.01)
  *G01N 21/64* (2006.01)
  *G01N 21/82* (2006.01)

(52) U.S. Cl.
  CPC ......... *G01N 21/0332* (2013.01); *G01N 21/05* (2013.01); *G01N 21/31* (2013.01); *G01N 21/645* (2013.01); *G01N 2021/3181* (2013.01); *G01N 2021/6482* (2013.01); *G01N 2021/6484* (2013.01); *G01N 2021/8557* (2013.01); *G01N 2201/0621* (2013.01); *G01N 2201/0624* (2013.01); *G01N 2201/0627* (2013.01); *G01N 2201/0668* (2013.01)

(56) References Cited

U.S. PATENT DOCUMENTS

| | | | |
|---|---|---|---|
| 2010/0047848 A1* | 2/2010 | Law | G01N 33/5005 435/29 |
| 2013/0161243 A1* | 6/2013 | Kanomata | G01N 21/05 210/85 |
| 2013/0187067 A1* | 7/2013 | Weiss | G01N 21/59 250/576 |
| 2016/0274074 A1* | 9/2016 | Fujiwara | G01N 21/41 |
| 2017/0089859 A1* | 3/2017 | Weiss | G01N 27/31 |
| 2018/0238845 A1* | 8/2018 | Eliason | G01N 30/74 |
| 2019/0302006 A1 | 10/2019 | Kono et al. | |
| 2022/0107261 A1* | 4/2022 | Nordman | G01N 21/01 |

* cited by examiner

FLOW CELL SYSTEM FOR OPTICAL FLUID ANALYSIS AND BIOREACTOR SYSTEM

BACKGROUND

The disclosed embodiments relate to a flow cell system for optical fluid analysis, and further to a bioreactor system comprising disposable bioreactor and a flow cell system for optical fluid analysis.

Optical detection systems for bioprocesses are commonly made for stainless steel reactors with probes, light guides and spectrometers. These systems are sterilizable in place by steam. However, this is not possible for disposable bioreactors, as they are commonly pre-sterilized by γ-radiation and a probe cannot be installed afterwards without breaking a sterile barrier.

Thus, it would be useful to have a flow cell system for an optical fluid analysis that has an improved sterilization behavior and/or that is capable of being used in a disposable bioreactor system.

SUMMARY

Disclosed herein is a flow cell system for optical fluid analysis comprising a disposable flow cell having a flow cell inlet, a flow cell outlet and at least one flow chamber comprising a fluid pathway, and at least one pair of opposed light transmitting windows arranged along the fluid pathway, an external flow cell holder for holding the flow cell, a first bypass line connectable to an apparatus containing a fluid to be analyzed and the flow cell inlet and a second bypass line connectable to said apparatus and the flow cell outlet, at least one light source, and an external detection device couplable with at least one of the flow cell holder and the flow cell for bringing the external detection device in optical communication with the flow cell, the device having at least one optical detection unit, wherein the external detection device is designed to conduct optical measurements of the fluid that flows in the flow cell through at least one pair of windows from externally under illumination by the at least one light source.

First of all, the flow cell is a disposable device. After conducting a measurement campaign, it may simply be disposed of. A sterilization for a later use is not required and the effort for providing a sterile flow cell in a measurement campaign is clearly reduced. However, if desired, it may also be sterilizable, such that it may be re-used.

The flow cell is designed for receiving flow of a fluid to be analyzed. For this purpose, it comprises a flow cell inlet, into which the fluid can enter the flow cell. It further comprises a flow cell outlet and a flow path that extends from the flow cell inlet to the flow cell outlet. The fluid to be analyzed flows along the flow path from the flow cell inlet to the flow cell outlet through the at least one flow chamber. Said flow chamber comprises a fluid pathway and at least one pair of opposed light transmitting windows. Such a flow chamber may comprise certain predetermined dimensions and characteristics that meet requirements to conduct certain optical measurements from outside the flow cell. For this, light may enter the respective flow chamber through the light transmitting windows and an optical measurement device is able to obtain optical information through the windows. Said optical information depend on the characteristics of the fluid as well as of the light. By analyzing the optical information, the characteristics of the fluid can be determined.

The windows may be made by a polymer, glass, fused silica, and other suitable materials. They allow to introduce light into a respective flow path through one of the windows. The light shines through the fluid and will be refracted, dampened and/or obscured over the flow path. These optical information for determining the characteristics of the fluid can thus be obtained through another one of the windows.

The flow cell is intended for being external to the apparatus containing the fluid to be examined. For this purpose, the external flow cell holder is provided, which holds the flow cell and compensates the gravity and inertia forces of the flow cell, the fluid and the bypass lines. By providing the holder, the flow cell is arranged at a precise location that allows to place the external detection device in a suitable position to the flow cell. At the same time, the external detection device is couplable with at least one of the flow cell holder and the flow cell. The term "couplable" may include any type of direct or indirect connection. For example, the external detection device may be coupled with the flow cell through a light guiding device wherein the external detection device is not necessarily mechanically connected to the holder.

The at least one light source could be realized in any suitable way, depending on the measurement process to be conducted. It may comprise one or a plurality of illumination sources for different types and wavelengths of light. It may also include a device for leading daylight from the surrounding into the respective flow path.

The external detection device is provided as one or a plurality of separate parts independent of the flow cell. Thus, the at least one optical detection unit, such as a sensor a camera for visible or invisible light or another device for measuring optical information is not directly integrated into the flow cell or the apparatus containing the fluid. Instead, the external detection device containing the at least one optical detection unit will be arranged exterior to the flow cell in a suitable position to the windows of the flow cell. While the flow cell holder may be configured for holding the external detection device, also the flow cell may comprise attachment elements or holders to fixate the external detection device. It may be possible to provide the external detection device with a housing that comprises a recess complementary shaped to the flow cell. Hence, the external detection device may be plugged onto the flow cell. For example, the flow cell may be enclosed in a plier-like manner by the housing of the external detection device to emit light on one side and receive optical information on the other side.

The first bypass line and the second bypass line are connectable to said apparatus and the flow cell. Consequently, the fluid to be analyzed flows through the first bypass line into the flow cell inlet and flows out from the flow cell outlet through the second bypass line and back into said apparatus. Consequently, the fluid to be analyzed is temporarily relocated externally to the apparatus, which enables the flow cell to be arranged outside of it. The bypass lines are connectable in a sterilized manner to said apparatus. They may for example be C-flex tubes, which can be sterilized together with the flow chamber before attachment.

The flow cell being an external part and being substantially free from measurement devices can be pre-sterilized after its manufacturing. Hence, the flow cell is a pre-sterilized chamber for optical measurements. It preserves sterility within the chamber for more than about two weeks and has no effects on living cells since the material is biocompatible. Due to its comparably simple design, it is producible with comparably low manufacturing costs. It can easily be adapted to different measurement processes and improves the measurement campaigns due to its flexible application. The flow cell system allows to analyze fluids in bioreactors, food processing systems, medical system or other apparatuses. The disposable flow cell is clamped into a reusable flow cell holder. Together with the light source and the external detection device is ensures a robust and reproducible setup for comparable measurements. By such a modular construction, particularly spectroscopic techniques, like UV/Vis, fluorescence, turbidity by scattered light, near infrared or Raman are possible, moreover microscopy is feasible.

Advantageously, the flow cell comprises a plurality of consecutive flow chambers, each having a single window, a pair of opposed windows, or a multitude of windows, wherein individual optical characteristics in the plurality of flow chambers differ from each other. The flow cell allows to obtain different optical information with a plurality of flow chambers adjusted to different measurement principles. For example, different pathway lengths, different light sources and different optical sensor devices are placeable at the flow cell and allow simultaneous measurements.

According to a further advantageous embodiment, individual distances between the opposed windows or an associated width of the respective flow chamber in the plurality of flow chambers differ from each other. The flow cell then offers a variety of flow chambers with distinct pathway lengths, i.e. said individual distance or width, for optical measurements of the fluid. For example, a light absorption behavior over the fluid can be measured along different pathway lengths simultaneously.

In a preferred embodiment, the system comprises at least one illumination source as the light source that emits light into one of a respective pair of windows. An illumination source may be any device that is capable of producing and emitting light, that enters into the flow cell through a respective window. The illumination source may be arranged in the flow cell holder, the external detection device or another external device that is capable of retaining the illumination source. It may also be feasible to include a plurality of illumination sources at any angle to the respective flow pathway for various measurement techniques.

Advantageously, the illumination source comprises at least one light emitting diode. A light emitting diode (LED) comprises a considerably compact design. LEDs are available with precisely tuned wavelengths or wavelength ranges. Depending on the desired measurements, certain LED can be chosen and integrated. Due to the compact design, the LED may simply be installed into the external detection device.

It is particularly advantageous, if the at least one light emitting diode comprises an array of light emitting diodes that emit light with different wavelengths. The array comprises at least two LEDs with distinct wavelengths chosen for meeting the required measurement. This choice may include excitation wavelengths of the most important analytes in the visible and non-visible range. As an example, but not as a limitation, wavelengths may be selected for the detection of Protein (260 nm, 280 nm), NaDH (340 nm) and Ribovlavin (450 nm). By triggering the different LEDs sequentially, the light is emitted with discrete wavelengths in a sequence. The external detection device may therefore exemplarily comprise a spectro(photo)meter. The array may be provided in a single or a plurality of LED units. The external detection device may also be used with spectrometers or spectrophotometers to investigate spectroscopic features and ranges in the UV, VIS, NIR, MIR and IR part of the light spectrum.

It is therefore preferred if the individual light emitting diodes of the array can be triggered independently to influence the light wavelength emitted into the respective flow chamber. This may be conducted manually by electromechanical switches, semi-automatically by electronic switches to be activated manually, or automatically by an electronic device. The electronic device may be a part of the external detection device and in electrical connection with the light emitting diodes.

A further advantageous embodiment comprises at least one wavelength dispersing device arranged between the at least one light source and the respective window for influencing the wavelength of the light supplied to the at least one flow chamber. The wavelength dispersing device may be a filter or prism device. The at least one wavelength dispersing device is capable of selecting one or multiple discrete wavelengths or a narrow band of wavelengths from a light source with a plurality of wavelengths. Resultantly, the characteristics of the light used for a respective flow chamber can be more precisely tuned to the requirements of an individual measurement. Of course, several filters couplable with a window of a flow chamber may be provided to be replaced during a measurement campaign.

In another embodiment, the system may comprise at least one light guiding device for guiding light from or to at least one of the windows. The at least one light source does not necessarily have to be placed directly at the respective window. This prevents heat emission into the flow cell by an illumination source or another type of light source. Also, ambient light may be collected and lead through the light guiding device. At the same time, the at least one optical detection unit may be coupled with a window of the flow cell through a light guiding device. This allows to compact the flow cell, as larger detection units can be placed away from the flow cell. The light guiding device may inter alia include glass fibers, liquid core waveguides or similar.

The flow cell may further comprise a flow deflection device arranged in the fluid pathway, such that fluid flowing in the fluid pathway impinges the flow deflection device, wherein the flow deflection device influences the flow direction of the fluid for mixing the fluid or for directing the fluid to an inner surface of at least one of the windows for cleaning said inner surface. Clogging of the respective surface may thus be prevented.

Furthermore, the at least one detection unit may be designed to conduct at least one optical analysis of a group of different types of optical analysis, the group comprising spectroscopic analysis, optical image recording, turbidity measurement, fluorescence measurement, absorption measurement, Raman measurement and scattering measurement. Spectroscopic analysis is briefly explained above and may include several types of spectroscopy. However, this may also include microscopy. For microscopic images, an optical lens system for focusing may be installed and a camera may be implemented as an optical detection unit. Image information may be evaluated by image processing algorithms. Scattering measurement may include particle scattering measurement to determine size or shape by using back reflection and transmission at various angles along with a statistical algorithm.

Turbidity can be measured in transmission or reflection in different angles. The required excitation wavelength can be determined depending on the application. The flow cell for turbidity measurements may include a minimum of three optical windows: one for light excitation and measuring scattered light in reflection, one in 180° angle for measuring the transmission and one in a further different angle to differentiate between absorption and scattering. Further detection at additional angles are possible to determine more details of the bio process, i.e. in case of the apparatus being a bioreactor. The external detection device for the turbidity measurement may include a set of three or more detectors, such as photodiodes. By evaluating the emission sequentially, all information about absorption and scattering can be used together.

For fluorescence measurements, the emission of a sample which is different to the excitation wavelength is investigated. Here several distinct wavelength combinations may be chosen depending on the fluorescence of the application. For example, LEDs from the above-mentioned UV/VIS measurement may be used. The external detection system may only need to be equipped with band pass filters to select the specific emission wavelengths.

In a further advantageous embodiment, the at least one detection unit comprises at least one optical path for the analysis of the fluid, which optical path is perpendicular to the respective fluid pathway. Thus, light is emitted perpendicularly to the fluid pathway and/or the respective detection unit is oriented perpendicularly to the fluid pathway.

However, it may also be advantageous, if the at least one detection unit comprises at least one optical path for the analysis of the fluid, which optical path is not perpendicular to the respective fluid pathway. Depending on the measurement technique, a perpendicular optical path may not be sufficient or applicable. For example, a turbidity measurement may be optimized by using three differently oriented optical paths, wherein one of them may be perpendicular to the fluid pathway.

An advantageous embodiment may further comprise a heating device thermally couplable with the flow cell for controlling a temperature of the flow cell. The temperature level inside the flow cell may for example precisely be adjusted to reproduce boundary conditions.

The flow cell may further comprise an additional segregated flow chamber in fluid communication with the fluid path for conducting an optical reference measurement. The flow chamber is segregated different than the flow of fluid. It may be used as a reference or standard, which can then be used for comparison with other measurements.

Furthermore, the flow cell may comprise an additional flow path guiding as a part of the at least one flow chamber for reducing the flow rate in the at least one flow chamber.

An advantageous embodiment further comprises at least one electrode having a first end and a second end, wherein the first end is arranged in an interior space of the at least one chamber, wherein the second end is arranged at an exterior and wherein a remaining section of the electrode is sealed from the interior space, and wherein the detection device is designed to apply an electrical voltage or an electrical current to the at least one electrode and/or to measure an electrical voltage, an electrical current, an electrical resistance and/or an impedance of the fluid.

If required, the flow cell may also be sterilizable by a chemical sterilizing process or by a Gamma sterilizing process. The flow cell may be sterilized together with the bypass lines. Due to the lack of electronic or other sensitive devices, this does not lead to a damage.

Still further, the external flow cell holder may be designed for holding the at least one light source and the optical detection device and for retaining the flow cell in a predetermined alignment to the at least one light source and the optical detection device.

The inventive embodiments disclosed herein further relate to a bioreactor system, comprising a disposable bioreactor and a flow cell system for optical fluid analysis, comprising a disposable flow cell having a flow cell inlet, a flow cell outlet and at least one flow chamber comprising a fluid pathway, and at least one pair of opposed light transmitting windows arranged along the fluid pathway, an external flow cell holder for holding the flow cell, a first bypass line connectable to the bioreactor containing a fluid to be analyzed and the flow cell inlet and a second bypass line connectable to the bioreactor and the flow cell outlet, at least one light source, and at least one external detection device couplable with at least one of the flow cell holder and the flow cell for bringing the external detection device in optical communication with the flow cell, the device having at least one optical detection unit, wherein the external detection device is designed to conduct optical measurements of the fluid that flows in the flow cell through at least one pair of windows from externally under illumination by the at least one light source.

BRIEF DESCRIPTION OF THE DRAWINGS

The present invention may be better understood, and its numerous objects and advantages will become apparent to those skilled in the art, by reference to the accompanying drawings wherein like reference numerals refer to like elements in the several figures and in which.

DETAILED DESCRIPTION

Figure 1:
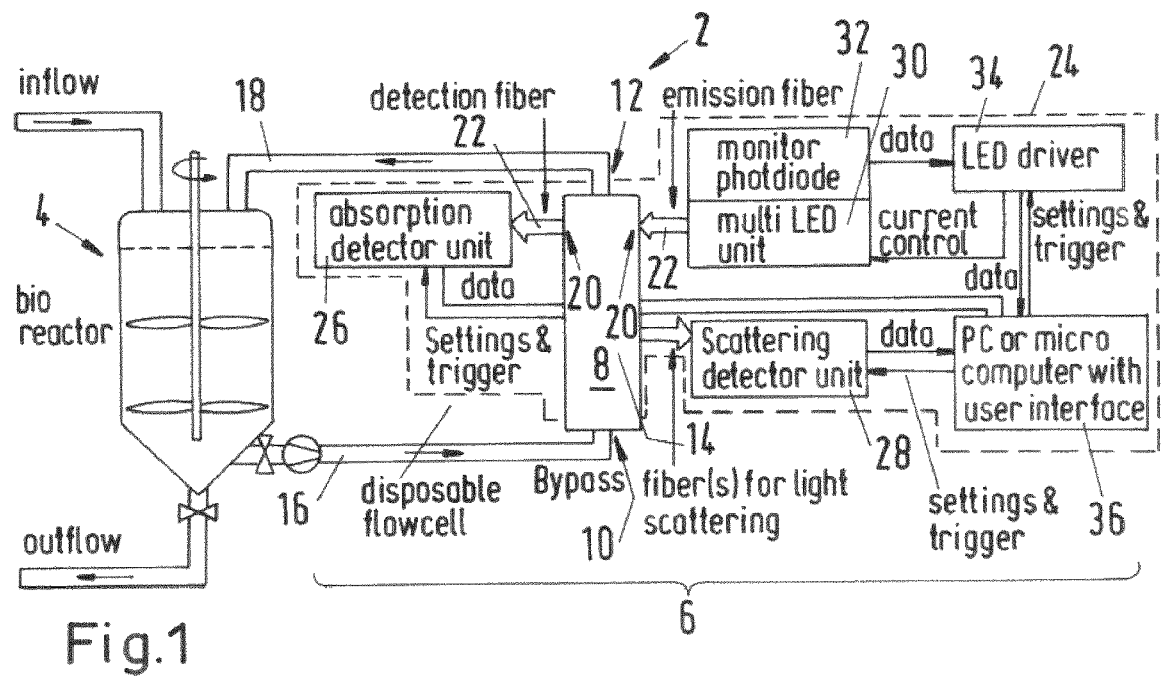
FIG. 1 is an overview on a bioreactor system.

FIG. 1 schematically shows a bioreactor system 2 comprising a disposable bioreactor 4 as well as a flow cell system 6 for an optical fluid analysis. In the bioreactor 4, a bio process is conducted. However, the bioreactor 4 may simply act as an example for an apparatus comprising containing a fluid to be analyzed.

The flow cell system 6 comprises a disposable flow cell 8 having a flow cell inlet 10 and a flow cell outlet 12. Between the flow cell inlet 10 and the flow cell outlet 12, at least one flow chamber 14 is provided, which is explained in further detail below. A first bypass line 16 is connected to the flow cell inlet 10, while a second bypass line 18 is collected with a flow cell outlet 12. Both bypass lines 16 and 18 are also connected to the bioreactor 4. Thus, fluid from the bioreactor 4 is guided into the disposable flow cell 8 and back into the bioreactor 4.

The flow chamber 14 exemplarily comprises a pair of opposed, light transmitting windows 20, which are coupled with light guiding devices 22. An external detection device 24 is coupled with the flow cell 8 for emitting light into one of the windows 20, and obtaining optical information through another one of the windows 20. Light is guided by the light guiding devices 22 for achieving this. The external detection device 24 is indicated with dashed lines and may include components that enable the system 2 to conduct the optical fluid analysis.

The external detection device exemplarily comprises an absorption detection unit 26 as well as a scattering detection unit 28. These are merely examples for one or several optical detection units integrated into the external detection device 24.

For an illumination of the fluid that flows through the flow chamber 14, exemplarily one or several LEDs 30 are provided, which emit light and illuminate the interior of the flow chamber 14 through the light guiding device 22. As an example, a monitoring photodiode 32 is provided, which monitors the frequency and brightness of the light that is emitted by the LEDs. Through an LED driver 34, the brightness and color of the light can be controlled. The intensity and frequency can be changed preferably for each LED 30. Several LEDs 30 can be combined to a multi-wavelength device. For example, this may be conducted by an electronics unit 36, such as a PC or a microcomputer, which is preferably equipped with a user interface. The electronics unit 36, the LED driver 34, the monitoring photodiode 32 and the LEDs 30 may or may not be a part of the external detection device 24, depending on the desired setup. If they are not a part of the external detection device 24, they may be provided separately.

The detection units 26 and 28 and the LED driver 34 are coupled with the electronic unit 36 and together lead to conducting the analysis. For example, these components may be integrated into the electronics unit 36 or they may be provided as one or multiple external devices, which are couplable with the electronics unit 36.

Figure 2:
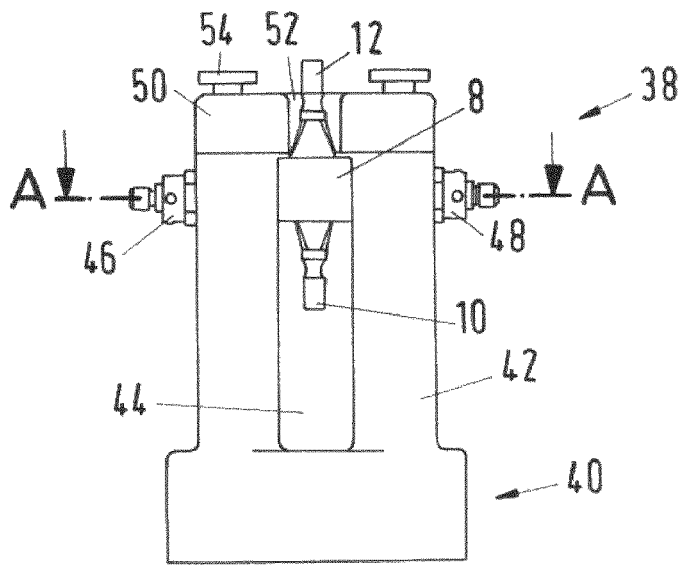
FIG. 2 is a first view and a first cross-sectional view onto the holder.
Figure 2:
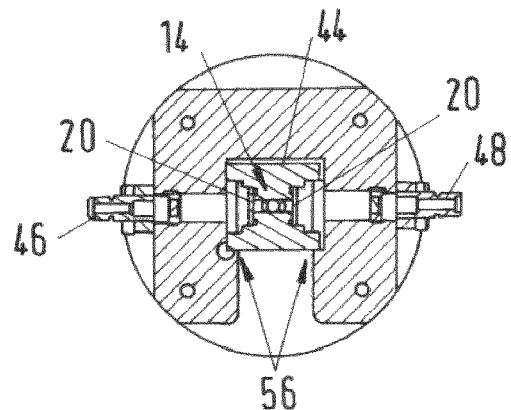

In FIG. 2, an external flow cell holder 38 is shown. It exemplarily comprises a base 40 for placing the holder 38 onto a table or another surface. The holder 38 comprises a housing 42 with a recess 44, which is designed to enclose the flow cell 8 in a plier-like manner. The flow cell inlet 10 and the flow cell outlet 12 are shown as a duct. At the sides of the housing 42, a first optical coupling 46 and a second optical coupling 48 are arranged. These are aligned with the opposed windows 20 of the flow cell 8 in its installed position. Here, the optical light guiding devices 22 illustrated in FIG. 1 can be attached.

At a top portion of the flow cell holder 38, a lid 50 is provided, which has an opening 52 for leading the flow cell outlet 12 through and for retaining the flow cell 8 in the recess 44. For this, the opening 52 has a smaller width than the recess 44. The lid 50 can be secured to the remaining part of the holder 38 by thumb screws 54, which are easy to release.

In the lower part of FIG. 2, a cross-sectional view indicated by the letters A is shown. Here, it is apparent that the flow cell 8 snugly fits into the recess 44. The flow chamber 14 provides a fluid pathway 15, which will be filled with the fluid to be analyzed. The two opposed windows 20 are in line with the flow chamber 14 and the optical couplings 46 and 48. In this view it can be seen that the holder 38 has a C-like cross-sectional surface in the section comprising the recess 44. The flow cell 8 can easily be taken out of the recess 44 and be disposed of and replaced. For retaining the flow cell 8 in a lateral direction, the recess 44 comprises undercuts 56.

Figure 3:
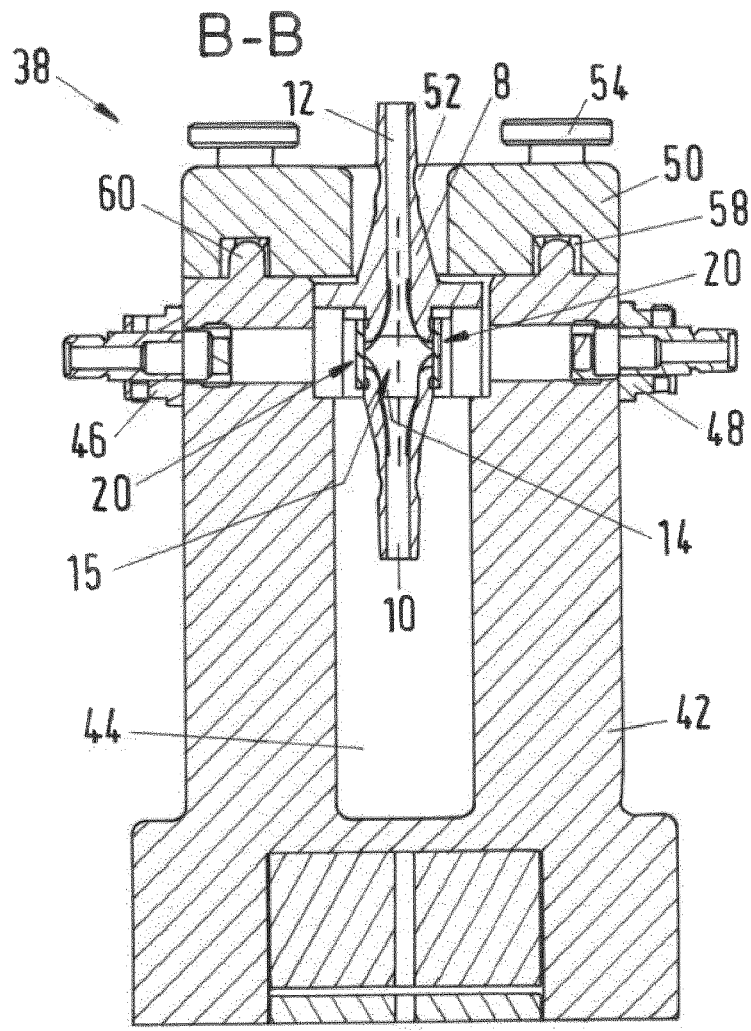
FIG. 3 is a second view and a second cross-sectional view onto the holder.
Figure 3:
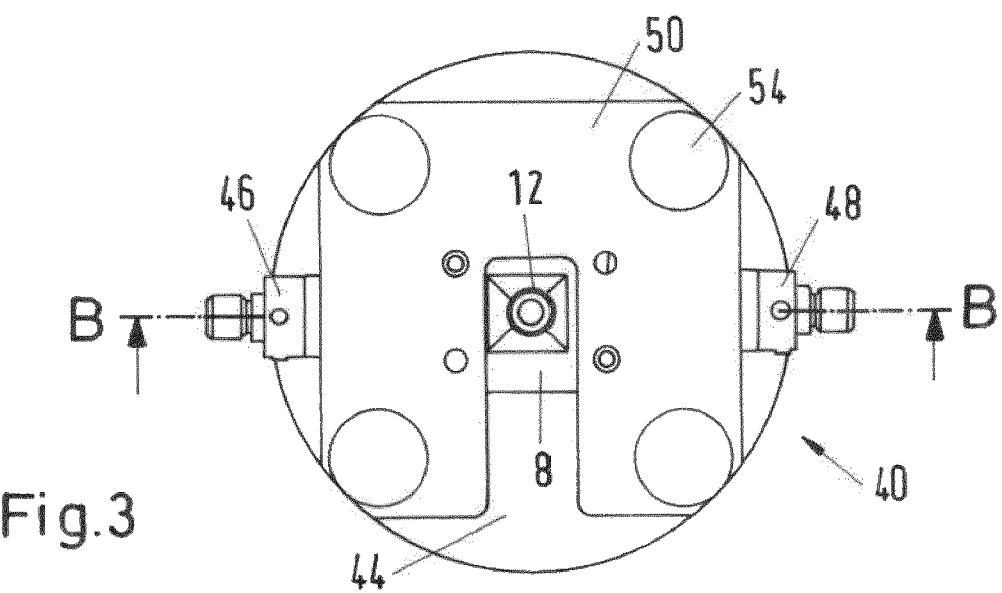

FIG. 3 shows a top view in the bottom section and a cross-sectional view of the holder 38 in the top section of the figure. The orientation of the cross-sectional view of the flow cell 8 and the holder 38 is indicated by the letters B in the top view. In the cross-sectional view, the holder 38 and the flow cell 8 are shown in detail. In the flow cell 8, the two opposed windows 20 are visible. The flow cell 8 may be a 3-D printed or casted part as a single piece, with the windows 20 being attached as separate parts. They may be made from another material for improving the optical characteristics and may be glued into the flow cell 8.

For aligning the lid 50, it comprises centering cavities 58, which are to be aligned with complimentary shaped centering protrusions 60. The optical couplings 46 and 48 may be screwed into the housing 42. The recess of 44 extends far below the flow cell inlet 10 for allowing to easily house a hose or duct that is attached to the flow cell inlet 10.

Figure 4:
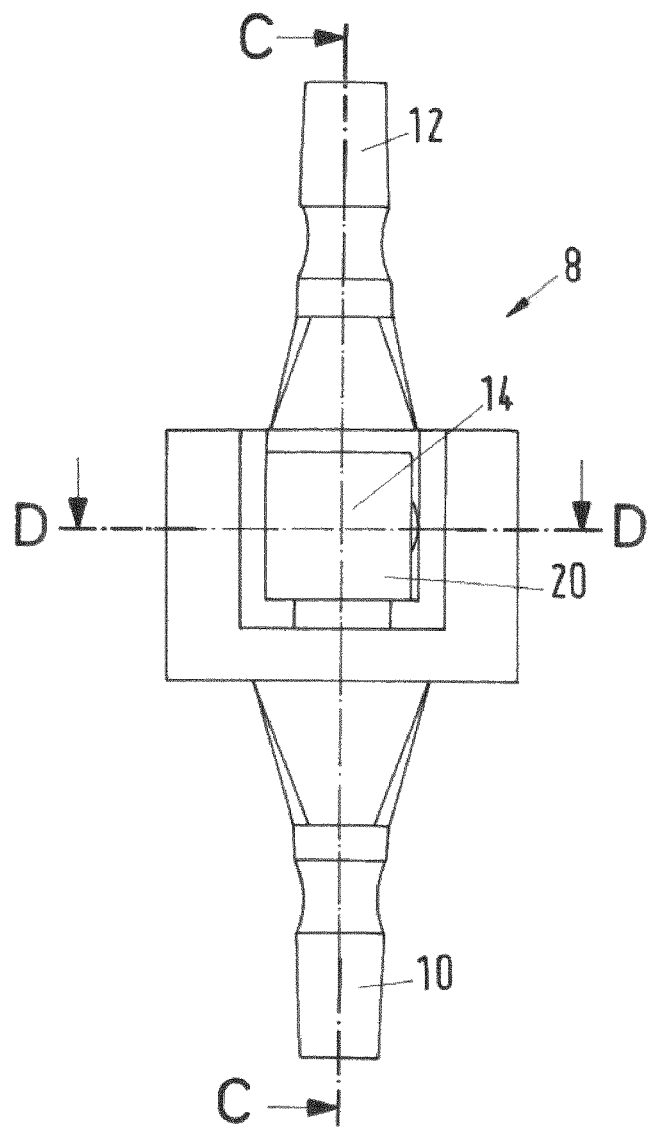
FIGS. 4 and 5 is the flow cell in a lateral view and two cross-sectional views.
Figure 4:
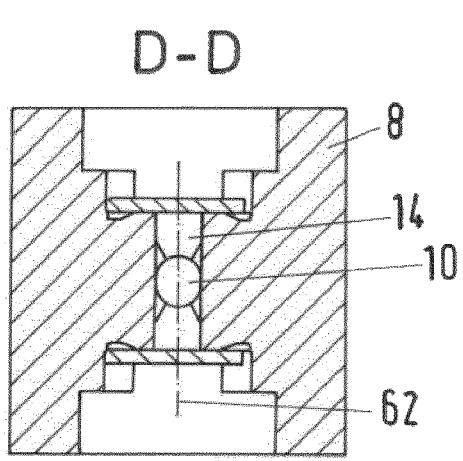
Figure 5:
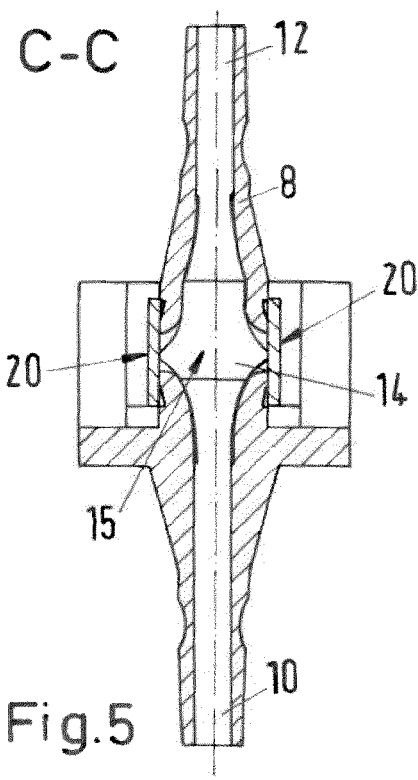

FIG. 4 shows the flow cell 8 in another perspective, from which the flow chamber 14 is visible. The translucent windows 20 are arranged parallel to the viewing plane of this figure and provide an optical axis 62, which in this case is perpendicular to the fluid pathway 15, which extends perpendicular to the viewing plane of FIG. 4 with regard of the cross-section at the bottom of FIG. 4. The viewing direction of an enlarged cross-sectional illustration at the bottom of the figure is indicated with the letters D. Here, it is possible to view from the flow chamber 14 through the flow cell inlet 10 downwards. FIG. 5 shows the flow cell 8 in a cross-sectional illustration, the viewing direction of which is indicated with the letters C in FIG. 4.

Figure 6:
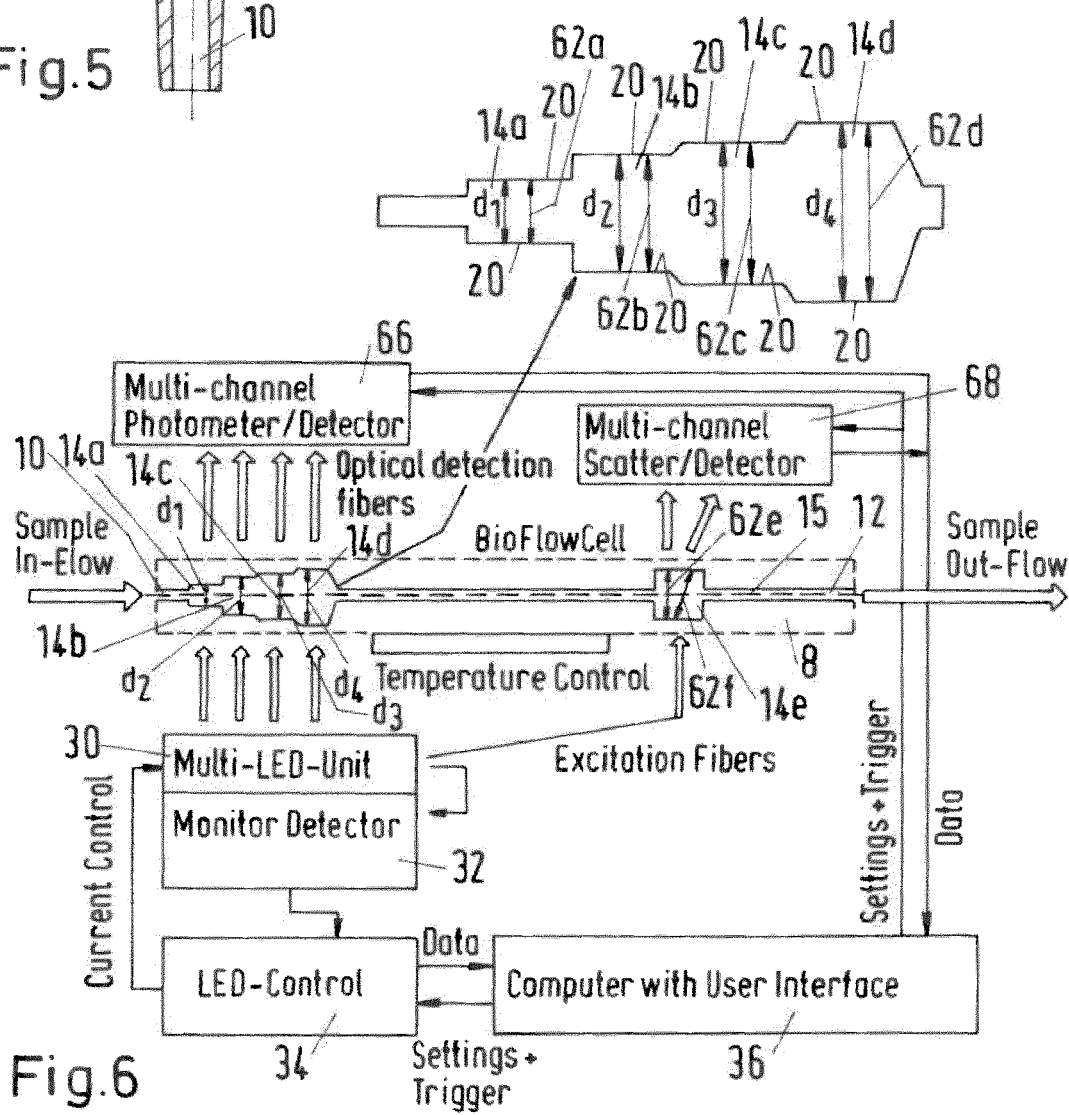
FIG. 6 is a further overview of the flow cell system.

FIG. 6 shows a part of the system 2 in a schematic overview. Here, the flow cell 8 is shown with a heating device 64, which is thermally coupled with the flow cell 8. The heating device 64 may be controllable in order to set and maintain a predetermined temperature in the flow cell 8. Further, the flow cell 8 is shown to comprise several consecutive flow chambers 14a, 14b, 14c and 14d, which are arranged along the fluid pathway 15. The fluid to be analyzed flows through the flow chambers 14a, 14b, 14c and 14d one after another. The flow chambers 14a, 14b, 14c and 14d each comprise a distance $d_1$, $d_2$, $d_3$ and $d_4$ between opposed windows 20, which differ from each other. In the example shown, the distances $d_1$, $d_2$, $d_3$ and $d_4$ increase along the flow pathway 15.

The light source 30 in the form of a multi LED unit emits light into the windows 20 of the flow chambers 14a, 14b, 14c and 14d. At an opposed side of the flow cell 8, the light leaves the respective windows 20 and is routed to a detection unit 66, which may exemplarily comprise a plurality of absorption detection units 26 or any other suitable detection units. By this, several optical paths 62a, 62b, 62c, 62d are created, which are perpendicular to the fluid pathway 15. This is further depicted in a magnified section in FIG. 6.

Further downstream, another flow chamber 14e is provided. Here, besides absorption detection, also a scattering detection may be conducted. Thus, there may be a perpendicular optical path 62e, as well as an optical path 62f, which is not perpendicular to the fluid pathway 15. A detection unit 68 may be provided, which is inter alia capable of providing the scattering detection.

Figure 7:
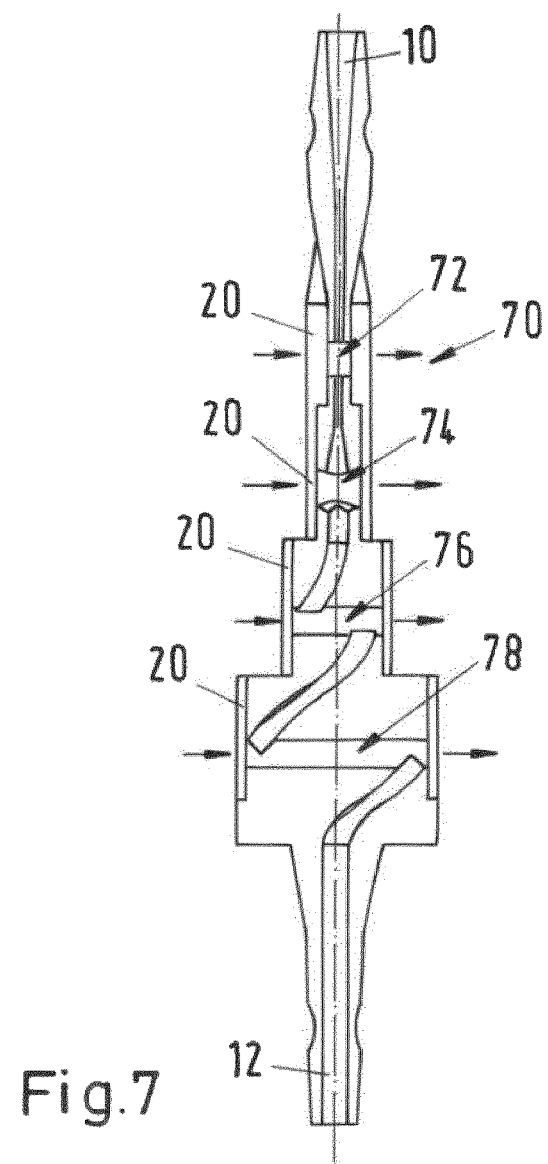
FIGS. 7 to 12 show further exemplary embodiments in various views.

FIG. 7 shows a multi-path-length absorption flow cell 70 with a plurality of fluid pathways 72, 74, 76 and 78, which are flown through in a consecutive manner by a fluid to be analyzed. In this particular example, the lengths of the pathways 72, 74, 76 and 78 increase successively. The second pathway 74 has a greater length than the first pathway 72. The length of the third pathway 76 exceeds the length of the second pathway 74 and so on. Merely as an example, the pathway lengths may be about 3 mm, 5 mm, 10 mm and 20 mm. Light is directed through the fluid pathways 72, 74, 76 and 78 as indicated with the arrows running from the left to the right in the viewing plane. Each fluid pathway 72, 74, 76 and 78 comprises a pair of translucent windows 20 are arranged parallel to each other and perpendicular to the respective fluid pathway 72, 74, 76 or 78, in analogy to the illustration in FIG. 5.

It is conceivable to provide other flow cells with another number of fluid pathways and/or different dimensions. Furthermore, the direction of flow may also be opposite, such that the pathways 72, 74, 76 and 78 with successively decreasing pathlengths are flown through. Also, the light emitted into the various fluid pathways 72, 74, 76 and 78 may comprise different wavelengths.

Figure 8:
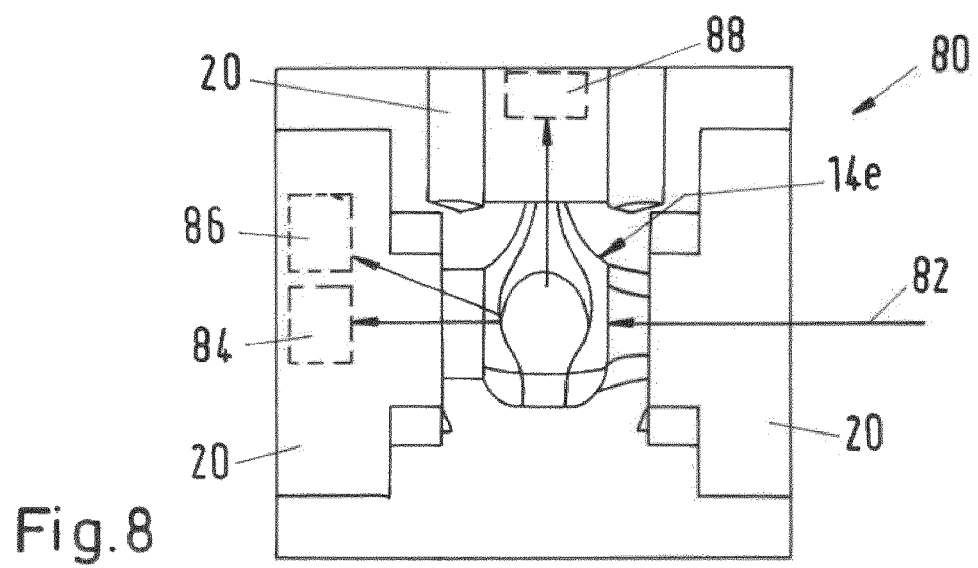

FIG. 8 shows a cross-sectional view of a flow cell 80, which may be the same as flow cell 8 of the previous figures and which may comprise the scattering flow chamber 14e indicated in FIG. 6. Here, the viewing plane is perpendicular to a main extension axis, in analogy to the indication D-D in FIG. 4. A ray of light 82, which may be emitted by an LED, in particular a laser LED, enters the flow chamber 14e and impinges onto the fluid to be analyzed. Three detection units are provided, which include a first detection unit 84 at an angle of 180° (shine through), a second detection unit 86 at an angle of 160° and a third detection unit 88 at an angle of 90°. Of cause, detection units may be other angles, when required. In analogy to the above, the detection units 84, 86 and 88 are provided externally and are thus only indicated by dashed lines for clarification. While the first detection units 84 is primarily provided for detecting light absorption, the second detection unit 86 and the third detection unit 88 are provided for detection of light scattering.

Figure 9:
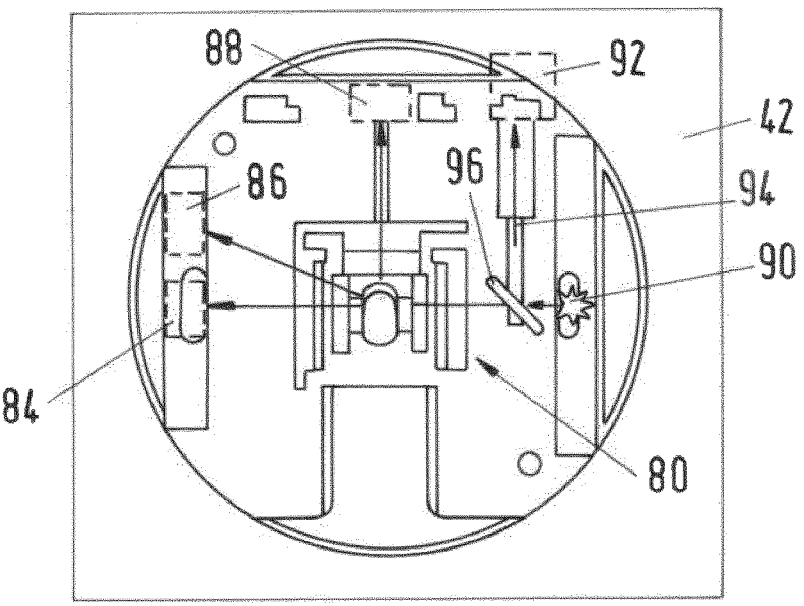

FIG. 9 shows the flow cell 80 held in the flow cell holder 38. Here, an LED 90 is provided to emit the ray of light 82 shown in FIG. 8. In addition to the flow cell 80, also a reference detection unit 92 is provided, onto which a reflected ray of light 94 is directed, which does not run through the fluid to be analyzed. Hence, a reference value may be generated to increase the detection accuracy. For this purpose, a mirror 96 is provided, which is partially transparent.

Figure 10:
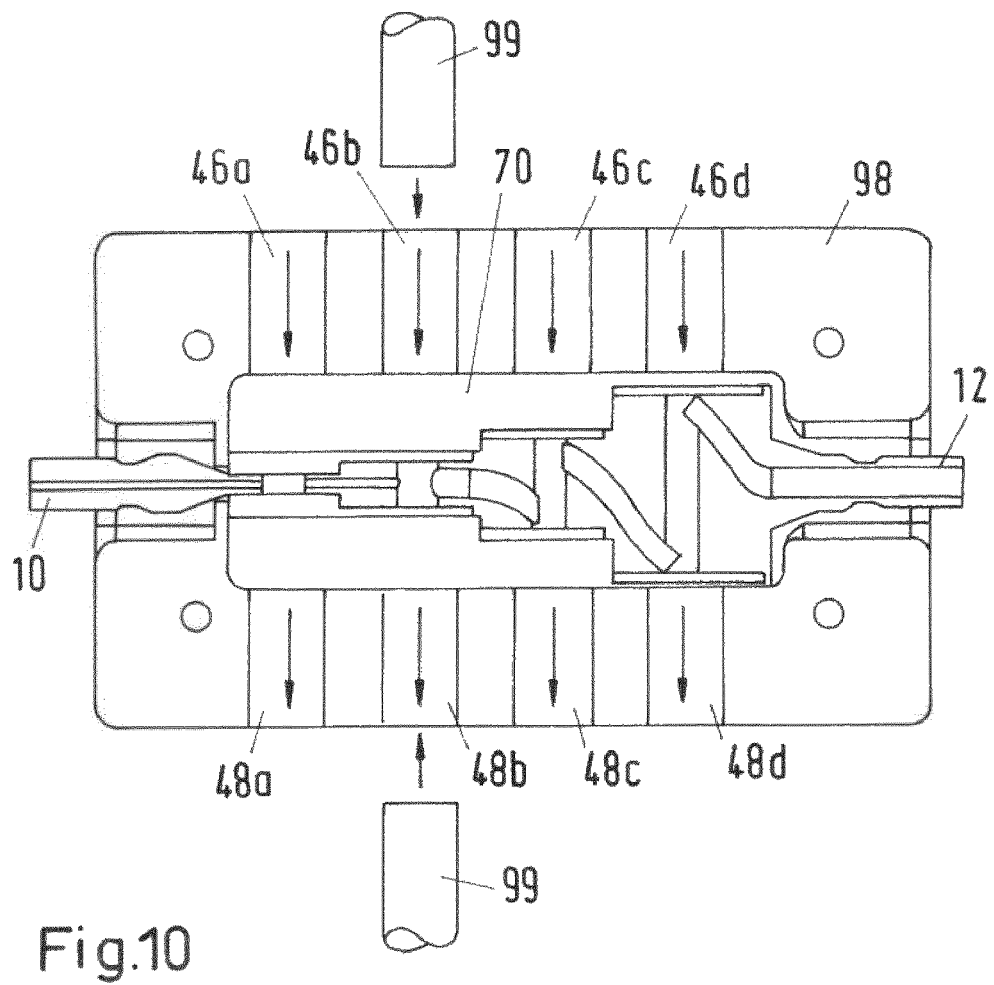

FIG. 10 shows a flow cell holder 98, which is exemplarily adapted for holding the flow cell 70 shown in FIG. 7. Here, the flow cell holder 98 comprises four first optical couplings 46a to 46d as well as four second optical couplings 48a to 48d. Here, the couplings 46a to 48d are merely illustrated as openings or seats for introducing dedicated devices for holding glass fibers 99, i.e. light guiding devices 22 (schematically illustrated), that lead light from an external light source to the flow cell or that lead light to an external detection unit for conducting the optical measurement. Also, the optical couplings 46a to 48d may be used for providing the respective light sources/LEDs or detection units.

Figure 11:
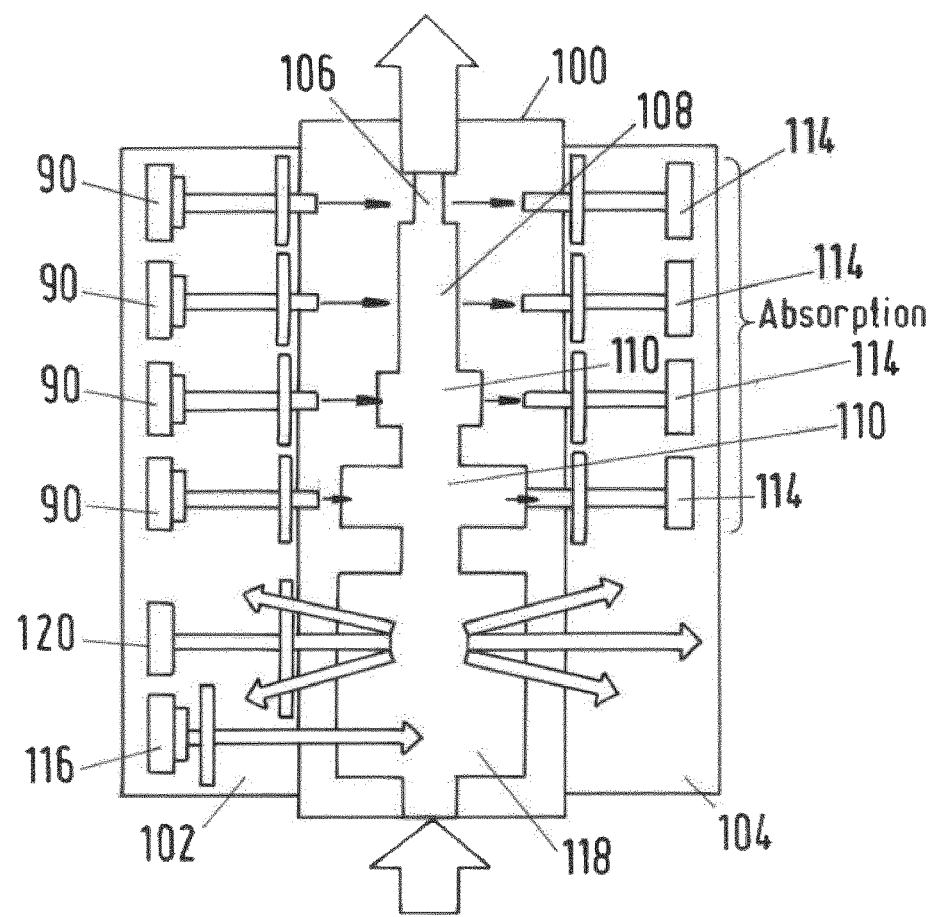

FIG. 11 shows a flow cell 100 together with a multi LED unit 102 as well as a detection device 104 having a plurality of detection units, in particular for providing turbidity measurements. The flow cell 100 comprises four fluid pathways 106, 108, 110 and 112, wherein each of the pathways 106 to 112 is associated with a light source 90 as well as a detection unit 114 in the form of a photo diode each for measuring absorption. Furthermore, a laser diode 116 is provided, which emits a laser into a section 118 of the flow cell, which leads to scattering the light. Here, a further detection unit 120 is provided, which is designed for measuring scattered light in an angle of 180° to the laser diode 116. Further detection units are possible, in analogy to FIG. 8.

Figure 12:
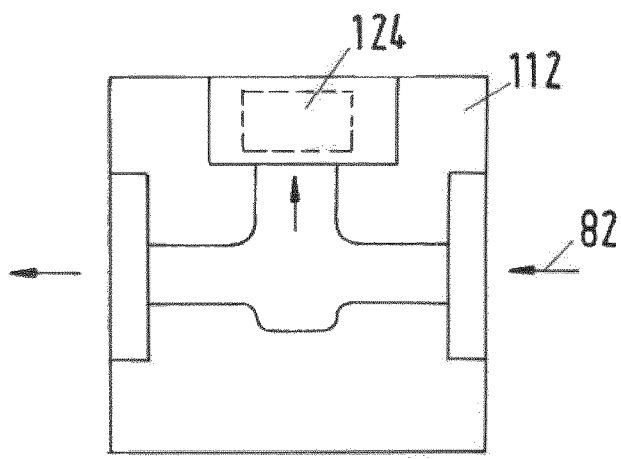

FIG. 12 shows another flow cell 122, which comprises a detection unit 124 for optical fluorescence measurement in an angle of 90° to a ray of light 82 entering the flow cell 122. Also, a detection unit 84 may be provided for detecting absorption, in analogy to FIG. 8.

The invention is not limited to one of the aforementioned embodiments, but can be modified in many ways.

All features and advantages resulting from the claims, the description and the figures, including constructive details, spatial arrangements and procedural steps, may be essential for the invention, both in themselves and in various combinations.

REFERENCE NUMERALS 2 bioreactor system
4 bioreactor/apparatus
6 flow cell system
8 disposable flow cell
10 flow cell inlet
12 flow cell outlet
14 flow chamber
15 fluid pathway
16 first bypass line
18 second bypass line
20 window
22 light guiding device
24 external detection device
26 absorption detection unit
28 scattering detection unit
30 LED/light source
32 monitoring photodiode
34 LED driver
36 electronics unit
38 flow cell holder
40 base
42 housing
44 recess
46, 46a-46d first optical coupling
48, 48a-48d second optical coupling
50 lid
52 opening
54 screw
56 undercut
58 centering cavity
60 centering protrusion
62, 62a, 62b, 62c, 62d, 62e, 62f optical axis
64 heating device
66 detection unit
68 detection unit
70 flow cell (absorption)
72 fluid pathway
74 fluid pathway
76 fluid pathway
78 fluid pathway
80 flow cell (scattering and absorption)
82 ray of light
84 first detection unit
86 second detection unit
88 third detection unit
90 LED/light source
92 reference detection unit
94 reflected ray of light
96 mirror
98 flow cell holder
100 flow cell
102 multi LED unit/light source
104 detection device
106 fluid pathway
108 fluid pathway 110 fluid pathway
112 fluid pathway
114 detection unit
116 laser diode/light source
118 section
120 detection unit
122 flow cell
124 detection unit
$d_1$, $d_2$, $d_3$ $d_4$ distance between opposed windows

The invention claimed is:

1. A flow cell system for optical fluid analysis, comprising:
- a disposable flow cell having a flow cell inlet with a fluid line connecting interface, a flow cell outlet with a fluid line connecting interface, and a fluid pathway comprising a plurality of consecutive flow chambers, with each of the consecutive flow chambers having individual optical characteristics that differ from each other;
- plural pairs of windows arranged along the fluid pathway, each pair of windows being associated with one of the consecutive flow chambers;
- an external flow cell holder being structured and arranged to hold the disposable flow cell so as to allow removal therefrom, wherein, when the disposable flow cell is held in the external flow cell holder, the fluid pathway and the flow cell inlet is housed within the external flow cell holder and at least a portion of the flow cell outlet is housed within the external flow cell holder;
- a first bypass line connectable to an apparatus containing a fluid to be analyzed and the flow cell inlet;
- a second bypass line connectable to said apparatus and the flow cell outlet;
- a light source comprising an array of light emitting diodes (LEDs) that emit light with different wavelengths, said LEDs being configured to be triggered independently to influence the wavelength of light emitted into a respective consecutive flow chamber; and
- an external detection device couplable with at least one of the flow cell holder and the flow cell for bringing the external detection device into optical communication with the flow cell, the external detection device having at least one optical detection unit,
- wherein the external detection device is configured to conduct optical measurements of fluid that flows in the flow cell through at least one pair of windows from externally underneath the illumination by the light source,
- wherein distances between the pairs of windows differ from each other along the fluid pathway.

2. The system of claim 1, further comprising at least one wavelength dispersing device arranged between the light source and the flow cell.

3. The system of claim 1, further comprising at least one light guiding device for guiding light from or to at least one of window of at least of the pairs of windows.

4. The system of claim 1, wherein the flow cell is adapted to utilize a flow deflection device.

5. The system of claim 1, wherein the at least one optical detection unit is configured to conduct at least one optical analysis from a group of optical analyses consisting of:
- spectroscopic analysis,
- optical image recording,
- turbidity measurement,
- fluorescence measurement,
- absorption measurement, and
- scattering measurement.

6. The system of claim 1, wherein the at least one optical detection unit comprises an optical path for the analysis of the fluid, the optical path being perpendicular to the fluid pathway.

7. The system of claim 1, wherein the at least one optical detection unit comprises an optical path for the analysis of the fluid, the optical path being other than perpendicular to the fluid pathway.

8. The system of claim 1, further comprising a heating device thermally couplable to the flow cell for controlling a temperature of the flow cell.

9. The system of claim 1, wherein the flow cell further comprises an additional segregated flow chamber in fluid communication with the fluid path for conducting an optical reference measurement.

10. The system of claim 1, wherein the fluid path of the flow cell further comprises a reduced flow rate section.

11. The system of claim 1, further comprising at least one electrode having a first end and a second end, wherein the first end is arranged in an interior space of the respective flow chambers, the second end is arranged at an exterior space, and a remaining section of the electrode is sealed from the interior space, and wherein the optical detection device is configured to perform one or more of:
   (i) applying an electrical voltage or an electrical current to the at least one electrode, and
   (ii) measuring one or more of an electrical voltage, an electrical current, an electrical resistance and an impedance of the fluid.

12. The system of claim 1, wherein the flow cell is sterilizable by a chemical sterilizing process or by a Gamma ray sterilizing process.

13. The system of claim 1, wherein the external flow cell holder is structured and arranged to have mounted thereto the light source and the optical detection device in a manner that allows the flow cell to be in a predetermined alignment to the light source and the optical detection device.

* * * * *